(12) United States Patent
Lin et al.

(10) Patent No.: US 7,763,582 B2
(45) Date of Patent: Jul. 27, 2010

(54) LOCALIZED INSULIN DELIVERY FOR BONE HEALING

(75) Inventors: Sheldon Suton Lin, Chatham, NJ (US);
Ankur Gandhi, Metuchen, NJ (US);
James Patrick O'Connor, Fanwood, NJ (US);
Loay A. Al-Zube, Zarga (JO);
Joseph Benevenia, Montclair, NJ (US);
J. Russell Parsons, Perth Amboy, NJ (US)

(73) Assignee: University of Medicine and Dentistry Of New Jersey, New Brunswick, NJ (US)

( * ) Notice: Subject to any disclaimer, the term of this patent is extended or adjusted under 35 U.S.C. 154(b) by 0 days.

(21) Appl. No.: 12/280,085

(22) PCT Filed: Feb. 21, 2007

(86) PCT No.: PCT/US2007/062521
§ 371 (c)(1),
(2), (4) Date: May 12, 2009

(87) PCT Pub. No.: WO2007/098479
PCT Pub. Date: Aug. 30, 2007

(65) Prior Publication Data
US 2009/0214468 A1 Aug. 27, 2009

Related U.S. Application Data

(60) Provisional application No. 60/775,076, filed on Feb. 21, 2006.

(51) Int. Cl.
*A61K 38/28* (2006.01)

(52) U.S. Cl. .............................. 514/3; 514/4
(58) Field of Classification Search ...................... None
See application file for complete search history.

(56) References Cited

U.S. PATENT DOCUMENTS 5,019,383 A * 5/1991 Hopp ...................... 424/194.1
5,061,286 A * 10/1991 Lyle ........................ 623/23.63

OTHER PUBLICATIONS

Millard D. J. Wound Care 4(8):343, 1995.*
Kagel EM, et al. Current Opinion in Orthopaedics 6(5):7-13, 1995.*
Wlldemann B, et al. Bone (34):862-868, 2004.*
Ghandi et al., "The Effects of Local Insulin Delivery on Diabetic Fracture Healing", Bone, Jul. 18, 2005, pp. 482-490, 37, Elsevier, Newark, New Jersey.
Cornish, J. et al., Insulin Increases Histomorphometric Indices of Bone Formation In Vivo, Calcif Tissue Intl, 1996, 59:492-495.
Gandhi, A. et al., The Effects of Local Insulin Delivery on Diabetic Fracture Healing, Bone, 2005, pp. 482-490.
Stuck, Walter G., The Effect of Insulin on the Healing of Experimental Fractures in the Rabbit, J. Bone Joint Surg Am., 1932, 14:109-115.

* cited by examiner

*Primary Examiner*—Robert Landsman
(74) *Attorney, Agent, or Firm*—Fox Rothscild LLP; Peter J. Butch, III; Vyacheslav Vasilyev (57) ABSTRACT

A method of promoting bone healing in a non-diabetic patient in need thereof by locally administering a therapeutically effective amount of insulin to the patient. A drug delivery device, which includes insulin and a pharmaceutically acceptable carrier, wherein the device is adapted for localized administration of insulin to a patient in need thereof is also presented.

23 Claims, 5 Drawing Sheets

Figure 1. Animal Health: BB Wistar Rats

| Blood Glucose Levels (mg/dl) | Day 1 | Day 3 |
|---|---|---|
| Non-diabetic (n=5) | 81.7±4.3 | 80.2±3.9 |
| Non-diabetic w/ insulin (n=6) | 83.1±5.1 | 82.5±4.4 |

Figure 2. Early fracture callus histology at 4 days in the A) non-diabetic and B) non-diabetic treated with insulin. Slides were stained with Weigerts iron hematoxylin, biebrich scarlet, and aniline blue (bone = blue; cartilage = red). C = cortical bone, OS = osteoid matrix, CC = proliferating chondrocytes, HC = hypertrophic chondrocytes.

Figure 3. Mechanical Testing: Sprague-Dawley Rats

|  | Torque to failure (Nmm) | Torsional Rigidity (Nmm/rad) | Bulk Modulus | Maximum Shear Stress (MPa) |
|---|---|---|---|---|
| Non-diabetic (n=6) | 77.5±39 | 3,437±1,953 | 98.6±51 | 8.3±3.4 |
| Non-diabetic w/ insulin (n=6) | 246.7±90 | 13,877±5,526 | 329±91 | 24±7 |
| p-value | 0.004 | 0.003 | 0.001 | 0.002 |

|  | Percent Torque to failure | Percent Torsional Rigidity | Percent Bulk Modulus | Percent Maximum Shear Stress |
|---|---|---|---|---|
| Non-diabetic (n=6) | 27±20 | 16±9.4 | 3.6±2.3 | 10.2±7.75 |
| Non-diabetic w/ insulin (n=6) | 43.7±15 | 49.5±17 | 10.5±3.3 | 15.6±5 |
| p-value | 0.144 | 0.004 | 0.003 | 0.126 |

The data represents average value ± standard deviation.

Figure 4. Mechanical Testing: BB Wistar rats

|  | Torque to failure (Nmm) | Torsional Rigidity (Nmm/rad) | Bulk Modulus | Maximum Shear Stress (Mpa) |
|---|---|---|---|---|
| Non-diabetic (n=5) | 178±38.1 | 9,363±5,032 | 235±102 | 18.7±3.4 |
| Non-diabetic w/ insulin (n=6) | 248±17 | 18,945±11,161 | 685±542 | 30.3±7.8 |
| p-value | 0.003 | 0.112 | 0.103 | 0.013 |

|  | Percent Torque to failure | Percent Torsional Rigidity | Percent Bulk Modulus | Percent Maximum Shear Stress |
|---|---|---|---|---|
| Non-diabetic (n=5) | 29.8±18 | 19.1±11.2 | 4.1±2.1 | 10.7±4.7 |
| Non-diabetic w/ insulin (n=6) | 36.3±8 | 44.6±27 | 13.3±9.6 | 15.6±5.2 |
| p-value | 0.537 | 0.080 | 0.066 | 0.247 |

The data represents average value ± standard deviation.

Figure 5. Insulin dosages

| Group | Dosage |
| --- | --- |
| Insulin Dose 1 | 0.1 ml of insulin-carrier mixture (0.8 g of carrier + 0.4 ml of 100 units/ml insulin) |
| Insulin Dose 2 | 0.1 ml of insulin-carrier mixture (0.8 g of carrier + 0.2 ml of 100 units/ml insulin) |

Figure 6. Local insulin levels

| Insulin levels normalized to total protein levels (pg/mg) | | Post-fracture time point | | |
| --- | --- | --- | --- | --- |
| Group Label | | 2 Days | 4 Days | 7 Days |
| Non-DM + TCP + insulin (dose 1) *Females* | Fractured femur | (n=5) 27± 6 | (n=4) 26± 7 | (n=4) 32 ± 4 |
| | Contralateral femur | 39 ± 14 | 51 ± 25 | 37 ± 17 |
| Non-DM + CaSo4 + insulin (dose 1) *Males* | Fractured femur | (n=4) 213 ± 69 | (n=2) $1.33 \times 10^3 \pm 1.2 \times 10^3$ | (n=4) 72 ± 22 |
| | Contralateral femur | 32 ± 21 | 24 ± 3 | 45 ± 20 |
| Non-DM + insulin-palmitic acid implant | Fractured femur | (n=6) 1.23 ± .35 | (n=6) 1.08 ± 0.26 | (n=6) 1.11 ± 0.24 |
| | Contralateral femur | 0.96 ± 0.24 | 0.84 ± 0.28 | 0.92 ± 0.32 |

Figure 7. Plasma insulin levels

| Plasma Insulin levels (pg/ml) | Post-fracture time point | | |
| --- | --- | --- | --- |
| Group Label | 2 Days | 4 Days | 7 Days |
| Non-DM + TCP + insulin (dose 1) Females | 442± 191 (n=5) | 306± 131 (n=4) | 305 ± 176 (n=4) |
| Non-DM + CaSo4 + insulin (dose 1) Males | 937 ± 670 (n=4) | 434 ± 107 (n=2) | 806 ± 454 (n=4) |
| Non-diabetic (no treatment) | 398 ± 14 (n=6) | 381 ± 15 (n=6) | 352 ± 11 (n=6) |

Figure 8. General health

| Blood Glucose Levels (mg/dl) | Day 2 | Day 4 | Day 7 |
| --- | --- | --- | --- |
| Non-DM + TCP + insulin (dose 1) Females | 95.7± 3.3 (n=5) | 86 ± 4 (n=4) | 90.2± 3 (n=4) |
| Non-DM + CaSo4 + insulin (dose 1) Males | 89± 4.6 (n=4) | 90 ± 2.1 (n=2) | 82.5± 2.2 (n=4) |

Figure 9. 4 Weeks Mechanical Testing: BB Wistar male rats, Liquid insulin with Tri-Calcium Phosphate

|  | Torque to failure (Nmm) | Torsional Rigidity (Nmm/rad) | Sheer Modulus | Maximum Shear Stress (Mpa) |
|---|---|---|---|---|
| Non-DM + TCP + saline (n=3) | 330 ± 126 | $40 \times 10^3 \pm 7.7 \times 10^3$ | $3.2 \times 10^3 \pm 1.9 \times 10^3$ | 78 ± 45 |
| Non-DM + TCP + insulin (n=3) (dose 2) | 402 ± 326 | $51.4 \times 10^3 \pm 32 \times 10^3$ | $3.8 \times 10^3 \pm 4.9 \times 10^3$ | 91 ± 115 |
| p-value | P > 0.6 | P > 0.6 | P > 0.6 | P > 0.6 |

The data represents average value ± standard deviation.

Figure 10. Mechanical Testing: BB Wistar male rats, Liquid insulin with Calcium Sulfate

|  | Torque to failure (Nmm) | Torsional Rigidity (Nmm/rad) | Sheer Modulus | Maximum Shear Stress (Mpa) |
|---|---|---|---|---|
| Non-DM + CaSo4 + saline (n=4) | 279 ± 197 | $30.6 \times 10^3 \pm 24 \times 10^3$ | 720 ± 541 | 24 ± 15 |
| Non-DM+CaSo4+ insulin ( dose 2) (n=2) | 514 ± 15 | $75 \times 10^3 \pm 702$ | $2.7 \times 10^3 \pm 880$ | 62 ± 18 |
| Non-DM+CaSo4+ insulin ( dose 1) (n=2) | 321 ± 46 | $34 \times 10^3 \pm 4.7 \times 10^3$ | $1.3 \times 10^3 \pm 233$ | 43 ± 7 |
| p-value dose 1 vs. control<br>p-value dose 2 vs. control | 0.28<br>0.2 | 0.054<br>0.034 | 0.21<br>0.32 | 0.56<br>0.79 |

The data represents average value ± standard deviation.

Figure 11. 6 weeks histomorphometry analysis. ISO: control non-diabetic rats received one third of blank-palmitic acid implant placed into the allograft segment. LISO: experimental, non-diabetic rats received one third of Insulin-palmitic acid implant placed into the allograft segment.

LOCALIZED INSULIN DELIVERY FOR BONE HEALING

CROSS REFERENCE TO RELATED APPLICATIONS

This application claims priority under 35 U.S.C. §19(e) to U.S. Provisional Application Ser. No. 60/775,076, which was filed on Feb. 21, 2006. The disclosure of this application is incorporated herein by reference.

BACKGROUND OF THE INVENTION

Fracture healing is a complex process that involves the sequential recruitment of cells and the specific temporal expression of factors essential for bone repair. The fracture healing process begins with the initial formation of a blood clot at the fracture site. Platelets and inflammatory cells within the clot release several factors that are important for chemotaxis, proliferation, angiogenesis and differentiation of mesenchymal cells into osteoblasts or chondroblasts.

The fracture healing process subsequent to the initial hematoma formation can be classified as primary or secondary fracture healing. Primary fracture healing occurs in the presence of rigid internal fixation with little to no interfragmentary strain resulting in direct bone formation across the fracture gap. Secondary fracture healing occurs in response to interfragmentary strain due to an absence of fixation or non-rigid fixation resulting in bone formation through intramembranous and endochondral ossification characterized by responses from the periosteum and external soft tissue.

Intramembranous bone formation originates in the periosteum. Osteoblasts located within this area produce bone matrix and synthesize growth factors, which recruit additional cells to the site. Soon after the initiation of intramembranous ossification, the granulation tissue directly adjacent to the fracture site is replaced by cartilage leading to endochondral bone formation. The cartilage temporarily bridging the fracture gap is produced by differentiation of mesenchymal cells into chondrocytes. The cartilaginous callus begins with proliferative chondrocytes and eventually becomes dominated by hypertrophic chondrocytes. Hypertrophic chondrocytes initiate angiogenesis and the resulting vasculature provides a conduit for the recruitment of osteoblastic progenitors as well as chondroclasts and osteoclasts to resorb the calcified tissue. The osteoblastic progenitors differentiate into osteoblasts and produce woven bone, thereby forming a united fracture. The final stages of fracture healing are characterized by remodeling of woven bone to form a structure, which resembles the original tissue and has the mechanical integrity of unfractured bone.

Studies have documented that diabetes impairs bone healing clinically and experimentally due to low insulin levels. For example, a novel intramedullary insulin delivery system was used in a diabetic femur fracture model to investigate the potential direct effects of insulin on bone healing. (See Gandhi, A., et al., "The effects of local insulin delivery on diabetic fracture healing," Bone, vol. 37(4), pp. 482-90 (2005).) However, Gandhi et al. does not rule out the possible normalization of blood glucose levels or reduction of advanced glycation endproducts (byproduct of hyperglycemia) in the local fracture environment. The use of a diabetic fracture model prevents a definitive conclusion from being reached regarding the anabolic effects of insulin.

A further study by Cornish, J., et al., "Insulin increases histomorphometric indices of bone formation in vivo," Calcif. Tissue Int., vol. 59(6), pp. 492-5 (1996), uses a non-diabetic intact calvarial animal model to investigate the effects of insulin on bone metabolism. However, the processes of bone metabolism are vastly different from bone repair. Bone metabolism is the interplay between bone formation and bone resorption. Bone repair, as described previously, is a complex process that involves the sequential recruitment and the differentiation of mesenchymal cells towards the appropriate osteoblastic/chondrogenic lineage to repair the fracture/defect site.

SUMMARY OF THE INVENTION

The present invention relates to the local administration of insulin as an anabolic agent to accelerate bone healing in a non-diabetic patient.

One aspect of the present invention provides a method of promoting bone healing in a non-diabetic patient in need thereof by locally administering a therapeutically effective amount of insulin to the patient. Another aspect of the invention relates to the use of insulin in the manufacture of a medicament for accelerating bone healing in a non-diabetic patient in need thereof characterized by a therapeutically effective amount of insulin for localized administration. An additional aspect of the present invention provides a drug delivery device, which includes insulin and a pharmaceutically acceptable carrier, wherein the device is adapted for localized administration of insulin to a patient in need thereof.

In one embodiment, the patient is afflicted with a bone condition selected from bone fracture, bone trauma, arthrodesis, and a bone deficit condition associated with post-traumatic bone surgery, post-prosthetic joint surgery, post-plastic bone surgery, post-dental surgery, bone chemotherapy treatment, congenital bone loss, post traumatic bone loss, post surgical bone loss, post infectious bone loss, allograft incorporation or bone radiotherapy treatment.

In another embodiment, the insulin is selected from regular insulin, isophane insulin, neutral protamine hagedorn (NPH) insulin, semilente insulin, lente insulin, ultralente insulin, insulin glargine, insulin lispro, and insulin aspart.

In another embodiment, the insulin is delivered via an insulin delivery system. In one embodiment, the insulin delivery system includes at least one biocompatible carrier. In another embodiment, the biocompatible carrier includes poly-lactic acid, poly-glycolic acid, copolymers of poly-lactic acid or poly-glycolic acid. In yet another embodiment, the biocompatible carrier includes at least one bioerodible fatty acid or a metal salt of a fatty acid. In an additional embodiment, the fatty acid is selected from palmitic acid, steric acid, oleic acid, myristic acid, and metal salts thereof.

In another embodiment, the carrier includes porous or non-porous calcium phosphate, porous or non-porous calcium phosphate, porous or non-porous hydroxyapatite, porous or non-porous tricalcium phosphate, porous or non-porous tetracalcium phosphate, porous or non-porous calcium sulfate, or a combination thereof.

In yet another embodiment, the insulin delivery system includes an article for implantation. In an additional embodiment, the insulin delivery system includes a coating on an article for implantation.

In another embodiment, the insulin delivery system includes a bioactive bone agent. An additional embodiment further includes contacting a site in the patient in need of bone healing with a therapeutically effective amount of a bioactive bone agent selected from peptide growth factors, anti-inflammatory factors, pro-inflammatory factors, inhibitors of apoptosis, MMP inhibitors and bone catabolic antagonists.

In another embodiment, the peptide growth factor is selected from IGF (1,2), PDGF (AA, AB, BB), BMPs, FGF (1-20), TGF-beta (1-3), aFGF, bFGF, EGF, VEGF, parathyroid hormone (PTH), and parathyroid hormone-related protein (PTHrP). In yet another embodiment, the anti-inflammatory factor is selected from anti-TNFα, soluble TNF receptors, IL1ra, soluble IL1 receptors, IL4, IL-10, and IL-13. In yet another embodiment, the bone catabolic antagonist is selected from bisphosphonates, osteoprotegerin, and statins.

An additional embodiment includes treating the patient with at least one procedure selected from bone autograft, bone allograft, autologous stem cell treatment, allogeneic stem cell treatment, chemical stimulation, electrical stimulation, internal fixation, and external fixation.

DETAILED DESCRIPTION OF THE INVENTION

This invention relates to a method of promoting bone healing in a non-diabetic patient in need thereof by locally administering a therapeutically effective amount of insulin to the patient. An additional embodiment includes the use of insulin in the manufacture of a medicament for accelerating bone healing in a non-diabetic patient in need thereof characterized by a therapeutically effective amount of insulin for localized administration.

Preferably, the patient in need of bone healing is afflicted with a bone condition selected from bone fracture, bone trauma, arthrodesis, and a bone deficit condition associated with post-traumatic bone surgery, post-prosthetic joint surgery, post-plastic bone surgery, post-dental surgery, bone chemotherapy treatment, congenital bone loss, post traumatic bone loss, post surgical bone loss, post infectious bone loss, allograft incorporation or bone radiotherapy treatment. Preferred sites of interest in the patient include sites in need of bone healing and areas adjacent and/or contiguous to these sites. Optionally, the treatment method of the present invention is combined with at least one procedure selected from bone autograft, bone allograft, autologous stem cell treatment, allogeneic stem cell treatment, chemical stimulation, electrical stimulation, internal fixation, and external fixation.

As used herein, the term "insulin" includes insulin, insulin variants, or compounds that mimic the function of insulin. The insulin may be derived from a human source, an animal source, a bacterial source, or a recombinant source. Preferred types of insulin include regular insulin (for example, Actrapid®, Velosulin®, Humulin S®, and Pur-In Neutral®), isophane insulin, neutral protamine hagedorn (NPH) insulin (for example, Insulatard®, Insulatard Ge®, Protophane®, Hypurin Isophane®, Pur-In Isophane®, Humulin I (Prb)®, and Humulin I®, semilente insulin, lente insulin, ultralente insulin, insulin glargine, insulin lispro, and insulin aspart.

Insulin is locally administered to the patient by injection of insulin or an insulin delivery system or surgical implantation of a drug delivery device adapted for the localized administration of insulin (e.g., an insulin delivery system). Therefore, the present invention also relates to a drug delivery device, which includes insulin and a pharmaceutically acceptable carrier, wherein the device is adapted for localized administration of insulin to a patient in need thereof.

Insulin delivery vehicles employable with the methods of the present invention are preferably in the form of therapeutic formulations. Additionally, lipofections or liposomes can also be used to deliver the insulin to the target area.

Therapeutic formulations of insulin in the insulin delivery systems employable in the methods of the present invention are prepared for storage by mixing the insulin having the desired degree of purity with optional pharmaceutically acceptable carriers, excipients, stabilizers, or enhancers of insulin activity (Remington's Pharmaceutical Sciences 16th edition, Osol, A. Ed. (1980)). Such therapeutic formulations can be in the form of lyophilized formulations or aqueous solutions. Acceptable biocompatible carriers, excipients, or stabilizers are nontoxic to recipients at the dosages and concentrations employed, and may include buffers, for example, phosphate, citrate, and other organic acids; antioxidants including ascorbic acid and methionine; preservatives (e.g. octadecyldimethylbenzyl ammonium chloride; hexamethonium chloride; benzalkonium chloride, benzethonium chloride; phenol, butyl or benzyl alcohol; alkyl parabens, for example, methyl or propyl paraben; catechol; resorcinol; cyclohexanol; 3-pentanol; and m-cresol); low molecular weight (less than about 10 residues) polypeptides; proteins, for example, serum albumin, gelatin, or immunoglobulins; hydrophilic polymers, for example, polyvinylpyrrolidone; amino acids, for example, glycine, glutamine, asparagine, histidine, arginine, or lysine; monosaccharides, disaccharides, and other carbohydrates including glucose, mannose, dextrins, or hyaluronan; chelating agents, for example, EDTA; sugars, for example, sucrose, mannitol, trehalose or sorbitol; salt-forming counter-ions, for example, sodium; metal complexes (e.g. Zn-protein complexes); and/or non-ionic surfactants, for example, TWEEN™, PLURONICS™ or polyethylene glycol (PEG).

In order for the formulations to be used in vivo administration, they must be sterile. The formulation may be readily rendered sterile by filtration through sterile filtration membranes, prior to or following lyophilization and reconstitution. The therapeutic formulations herein preferably are placed into a container having a sterile access port, for example, an intravenous solution bag or vial having a stopper pierceable by a hypodermic injection needle.

The formulations used herein may also contain more than one active compound as necessary for the particular indication being treated, preferably those with complementary activities that do not adversely affect each other. Alternatively, or in addition, the formulation may comprise a cytotoxic agent, cytokine or growth inhibitory agent. Such molecules are present in combinations and amounts that are effective for the intended purpose.

Optionally, the insulin delivery system includes a bioactive bone agent in addition to insulin. Preferably, the bioactive bone agent is selected from peptide growth factors (e.g., IGF (1,2), PDGF (AA, AB, BB), BMPs, FGF (1-20), TGF-beta (1-3), aFGF, bFGF, EGF, VEGF, parathyroid hormone (PTH), and parathyroid hormone-related protein (PTHrP)), anti-inflammatory factors (e.g., anti-TNFα, soluble TNF receptors, IL1ra, soluble IL1 receptors, IL4, IL-10, and IL-13), pro-inflammatory factors, inhibitors of apoptosis, MMP inhibitors and bone catabolic antagonists (e.g., bisphosphonates, osteoprotegerin, and statins).

The route of administration of insulin via the insulin delivery system is in accordance with known methods, e.g., via immediate-release, controlled-release, sustained-release, or extended-release means. Preferred modes of administration for the insulin delivery system include injection directly into afflicted bone sites and areas adjacent and/or contiguous to these sites or surgical implantation of the insulin delivery system directly into afflicted bone sites and areas adjacent and/or contiguous to these sites. Alternatively, the insulin delivery system is an article for implantation or a coating on an article for implantation. Preferred forms for the insulin delivery system include powders, granules, and bone cements.

The insulin molecules may also be entrapped in microcapsules prepared, for example by coacervation techniques or by interfacial polymerization, for example, hydroxymethylcellulose or gelatin-microcapsules and poly-(methylmethacrylate) microcapsules, respectively. Such preparations can be administered in colloidal drug delivery systems (for example, liposomes, albumin microspheres, microemulsions, nanoparticles and nanocapsules) or in macroemulsions. Such techniques are disclosed in Remington's Pharmaceutical Sciences, 16th Edition (or newer), Osol A. Ed. (1980).

Optionally, the insulin delivery vehicle includes porous or non-porous calcium phosphate, porous or non-porous calcium phosphate, porous or non-porous hydroxyapatite, porous or non-porous tricalcium phosphate, porous or non-porous tetracalcium phosphate, porous or non-porous calcium sulfate, calcium minerals obtained from natural bone, inorganic bone, organic bone, or a combination thereof.

Where sustained-release or extended-release administration of insulin polypeptides is desired, microencapsulation is contemplated. Microencapsulation of recombinant proteins for sustained release has been successfully performed with human growth hormone (rhGH), interferon-, -, - (rhIFN-, -, -), interleukin-2, and MN rgp120. Johnson et al., Nat. Med. 2: 795-799 (1996); Yasuda, Biomed. Ther. 27: 1221-1223 (1993); Hora et al., Bio/Technology 8: 755-758 (1990); Cleland, "Design and Production of Single Immunization Vaccines Using Polylactide Polyglycolide Microsphere Systems" in Vaccine Design: The Subunit and Adjuvant Approach, Powell and Newman, eds., (Plenum Press: New York, 1995), pp. 439-462; WO 97/03692, WO 96/40072, WO 96/07399 and U.S. Pat. No. 5,654,010.

Suitable examples of sustained-release preparations include semipermeable matrices of solid hydrophobic polymers containing the insulin, which matrices are in the form of shaped articles, e.g. films, or microcapsules. Examples of sustained-release matrices include one or more polyanhydrides (e.g., U.S. Pat. Nos. 4,891,225; 4,767,628), polyesters, for example, polyglycolides, polylactides and polylactide-co-glycolides (e.g., U.S. Pat. No. 3,773,919; U.S. Pat. No. 4,767,628; U.S. Pat. No. 4,530,840; Kulkami et al., Arch. Surg. 93: 839 (1966)), polyamino acids, for example, polyl-ysine, polymers and copolymers of polyethylene oxide, polyethylene oxide acrylates, polyacrylates, ethylene-vinyl acetates, polyamides, polyurethanes, polyorthoesters, polyacetylnitriles, polyphosphazenes, and polyester hydrogels (for example, poly(2-hydroxyethyl-methacrylate), or poly (vinylalcohol)), cellulose, acyl substituted cellulose acetates, non-degradable polyurethanes, polystyrenes, polyvinyl chloride, polyvinyl fluoride, poly(vinylimidazole), chlorosulphonated polyolefins, polyethylene oxide, copolymers of L-glutamic acid and .gamma.-ethyl-L-glutamate, non-degradable ethylene-vinyl acetate, degradable lactic acid-glycolic acid copolymers, for example, the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of insulin for over 100 days, certain hydrogels release proteins for shorter time periods. Additional non-biodegradable polymers which may be employed are polyethylene, polyvinyl pyrrolidone, ethylene vinylacetate, polyethylene glycol, cellulose acetate butyrate and cellulose acetate propionate.

Alternatively, sustained-release formulations may be composed of degradable biological materials, for example, bioerodible fatty acids or metal salts thereof (e.g., palimitic acid, steric acid, oleic acid, myristic acid, metal salts thereof, and the like). Biodegradable polymers are attractive drug formulations because of their biocompatibility, high responsibility for specific degradation, and ease of incorporating the active drug into the biological matrix. For example, hyaluronic acid (HA) may be crosslinked and used as a swellable polymeric delivery vehicle for biological materials. U.S. Pat. No. 4,957, 744; Valle et al., Polym. Mater. Sci. Eng. 62: 731-735 (1991). HA polymer grafted with polyethylene glycol has also been prepared as an improved delivery matrix which reduced both undesired drug leakage and the denaturing associated with long term storage at physiological conditions. Kazuteru, M., J. Controlled Release 59:77-86 (1999). Additional biodegradable polymers which may be used are poly(caprolactone), polyanhydrides, polyamino acids, polyorthoesters, polycyanoacrylates, poly(phosphazines), poly(phosphodiesters), polyesteramides, polydioxanones, polyacetals, polyketals, polycarbonates, polyorthocarbonates, degradable and non-toxic polyurethanes, polyhydroxylbutyrates, polyhydroxyvalerates, polyalkylene oxalates, polyalkylene succinates, poly(malic acid), chitin, and chitosan.

Alternatively, biodegradable hydrogels may be used as controlled-release materials for the insulin delivery vehicles. Through the appropriate choice of macromers, membranes can be produced with a range of permeability, pore sizes and degradation rates suitable for different types of insulin.

Alternatively, sustained-release delivery systems for insulin can be composed of dispersions. Dispersions may further be classified as either suspensions or emulsions. In the context of delivery vehicles for insulin, suspensions are a mixture of very small solid particles which are dispersed (more or less uniformly) in a liquid medium. The solid particles of a suspension can range in size from a few nanometers to hundreds of microns, and include microspheres, microcapsules and nanospheres. Emulsions, on the other hand, are a mixture of two or more immiscible liquids held in suspension by small quantities of emulsifiers. Emulsifiers form an interfacial film between the immiscible liquids and are also known as surfactants or detergents. Emulsion formulations can be both oil in water (o/w) wherein water is in a continuous phase while the oil or fat is dispersed, as well as water in oil (w/o), wherein the oil is in a continuous phase while the water is dispersed. One example of a suitable sustained-release formulation is disclosed in WO 97/25563. Additionally, emulsions for use with insulin in the present invention include multiple emulsions, microemulsions, microdroplets and liposomes. Microdroplets are unilamellar phospholipid vesicles that consist of a spherical lipid layer with an oil phase inside. E.g., U.S. Pat. No. 4,622,219 and U.S. Pat. No. 4,725,442. Liposomes are phospholipid vesicles prepared by mixing water-insoluble polar lipids with an aqueous solution.

Alternatively, the sustained-release formulations of insulin may be developed using poly-lactic-coglycolic acid (PLGA), a polymer exhibiting a strong degree of biocompatibility and a wide range of biodegradable properties. The degradation products of PLGA, lactic and glycolic acids, are cleared quickly from the human body. Moreover, the degradability of this polymer can be adjusted from months to years depending on its molecular weight and composition. For further information see Lewis, "Controlled Release of Bioactive Agents from Lactide/Glycolide polymer," in Biogradable Polymers as Drug Delivery Systems M. Chasin and R. Langeer, editors (Marcel Dekker: New York, 1990), pp. 1-41.

When encapsulated insulin polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The encapsulated insulin polypeptides or insulin polypeptides in extended-release formulation may be imparted by formulating the insulin polypeptide with "water-soluble polyvalent metal salts," which are non-toxic at the release concentration and temperature. Exemplary "polyvalent metals" include the following cations: $Ca^{2+}$, $Mg^{2+}$, $Zn^{2+}$, $Fe^{2+}$, $Fe^{3+}$, $Cu^{2+}$, $Sn^{2+}$, $Sn^{4+}$, $Al^{2+}$ and $Al^{3+}$. Exemplary anions which form water-soluble salts with the above polyvalent metal cations include those formed by inorganic acids and/or organic acids. Such water-soluble salts have a solubility in water (at 20° C.) of at least about 20 mg/ml, alternatively 100 mg/ml, alternatively 200 mg/ml.

Suitable inorganic acids that can be used to form the "water soluble polyvalent metal salts" include hydrochloric, sulfuric, nitric, thiocyanic and phosphoric acid. Suitable organic acids that can be used include aliphatic carboxylic acid and aromatic acids. Aliphatic acids within this definition may be defined as saturated or unsaturated $C_{2-9}$ carboxylic acids (e.g., aliphatic mono-, di- and tri-carboxylic acids). For example, exemplary monocarboxylic acids within this definition include the saturated $C_{2-9}$ monocarboxylic acids acetic, proprionic, butyric, valeric, caproic, enanthic, caprylic pelargonic and capryonic, and the unsaturated $C_{2-9}$ monocarboxylic acids acrylic, propriolic methacrylic, crotonic and isocrotonic acids. Exemplary dicarboxylic acids include the saturated $C_{2-9}$ dicarboxylic acids malonic, succinic, glutaric, adipic and pimelic, while unsaturated $C_{2-9}$ dicarboxylic acids include maleic, fumaric, citraconic and mesaconic acids. Exemplary tricarboxylic acids include the saturated $C_{2-9}$ tricarboxylic acids tricarballylic and 1,2,3-butanetricarboxylic acid. Additionally, the carboxylic acids of this definition may also contain one or two hydroxyl groups to form hydroxy carboxylic acids. Exemplary hydroxy carboxylic acids include glycolic, lactic, glyceric, tartronic, malic, tartaric and citric acid. Aromatic acids within this definition include benzoic and salicylic acid.

Commonly employed water soluble polyvalent metal salts which may be used to help stabilize the encapsulated insulin polypeptides of this invention include, for example: (1) the inorganic acid metal salts of halides (e.g., zinc chloride, calcium chloride), sulfates, nitrates, phosphates and thiocyanates; (2) the aliphatic carboxylic acid metal salts calcium acetate, zinc acetate, calcium proprionate, zinc glycolate, calcium lactate, zinc lactate and zinc tartrate; and (3) the aromatic carboxylic acid metal salts of benzoates (e.g., zinc benzoate) and salicylates.

"Therapeutically-effective amount" means an amount effective to accelerate bone healing in a patient. Exemplary healing mechanisms include, but are not limited to: (a) retaining mineralized components in bone, (b) inhibiting release of mineralized components from bone, (c) stimulating osteoblast activity, (d) reducing osteoclast activity, or (e) stimulating bone remodeling.

Dosages of insulin employable with the present invention may vary depending on the particular use envisioned. The determination of the appropriate dosage or route of administration is well within the skill of an ordinary physician.

For example, when in vivo administration of insulin is employed, normal dosage amounts may vary from about 10 ng/kg up to about 100 mg/kg of mammal body weight or more per day, preferably about 1 g/kg/day to 10 mg/kg/day, depending upon the route of administration. Guidance as to particular dosages and methods of delivery is provided in the literature; see, for example, U.S. Pat. No. 4,657,760; 5,206,344 or 5,225,212. It is anticipated that different formulations will be effective for different treatments and different disorders, and that administration intended to treat a specific bone site or condition, may necessitate delivery in a manner different from that for another site or condition.

The following non-limiting examples set forth hereinbelow illustrate certain aspects of the invention.

EXAMPLES

Example 1

Materials and Methods

Animal Model

Male Sprague-Dawley rats were purchased from Charles River Laboratories (Wilmington, Mass.). Male BB Wistar rats were obtained from the breeding colony established at UMDNJ-New Jersey Medical School Research Animal Facility derived originally from Health Canada Animal Research Division (Ottawa, Canada). The rats were housed under controlled environmental conditions and fed ad libitum. All research protocols were approved by the Institutional Animal Care and Use Committee at UMDNJ-New Jersey Medical School.

Two experimental groups were used for each species of rat: i) control, non-diabetic rats received 0.2 ml of saline injected into the intramullary canal and ii) control, non-diabetic rats received 0.2 ml of ultralente insulin (5 units) injected into the intramedullary canal. On post-surgical days 1 and 3, blood obtained from the tail vein was tested for blood glucose levels (ACCU-CHEK Advantage, Roche Diagnostics, Indianapolis, Ind.).

Fracture Model

A closed mid-diaphyseal fracture was created in the right femur using the following modification of the methods described in Bonnarens, F., and Einhorn, T. A., "Production of a standard closed fracture in laboratory animal bone," J. Orthop. Res., vol. 2, pages 97-101 (1984). Once a medial, parapatellar incision was made, the patella was dislocated laterally and the interchondylar notch of the distal femur was exposed. An entry hole was made with an 18 gauge needle and the femur was reamed. A 16 gauge teflon cannula was then inserted into the intramedullary canal to stabilize the fracture while a closed midshaft fracture was created unilaterally with the use of a three-point bending, Einhorn fracture machine. Once the fracture was created, the cannula was removed and replaced with a 1.2 mm hollow rod in the Sprague-Dawley rats and a 1 mm Kirschner wire in the BB Wistar rat. Only animals that exhibited non-comminuted, transverse fractures, confirmed by radiographs, were used in this study. The animals were allowed to ambulate freely immediately post-fracture.

Qualitative Histology

The fractured femora were resected at day 4, decalcified, embedded and sectioned using standard histological techniques. To identify cartilage formation, sections were stained with Accustain™ Trichrome Staining kit (Masson, Sigma Diagnostics, St. Louis, Mo.) for histologic observation. The staining procedure consisted of fixing the sections in Accustain™ Bouins solution (Sigma Diagnostics, St. Louis, Mo.) overnight. Bouins solution enhances the cross linking of proteins within the section to help ensure that the morphology of the sample is maintained for subsequent histologic viewing. The trichrome consists of Weigerts Iron Hematoxylin (Sigma Diagnostics, St. Louis, Mo.), biebrich scarlet and analine blue. Hematoxylin is a general nuclear stain, biebrich scarlet stains cytoplasm and muscle and finally, collagen is stained with analine blue. Rinsing the samples in acetic acid following the staining procedure, allows for more delicate and transparent colors. Tissue corresponding to bone appears blue and cartilage appears red. The fracture callus was defined as the region located on either side of the cortices, external to the intramedullary marrow cavity. The samples were viewed and digital photomicrographs were made using an Olympus BH2-RFCA microscope (Olympus Optical Co., Ltd., Shinjuku-ku, Tokyo, Japan) and a Polaroid DMC1e digital camera (Polaroid, Waltham, Mass.).

Mechanical Testing

Fractured and contralateral femora were resected at 4 weeks and cleaned of soft tissue. Femora were cleaned of soft tissue and the intramedullary rod was removed. Samples were wrapped in saline (0.9% NaCl) soaked gauze and stored at −20° C. Prior to testing, all femora were removed from the freezer and allowed to thaw to room temperature for three to four hours. The proximal and distal ends of the fractured and contralateral femora were embedded in Wood's metal. Torsional testing was conducted using a servohydraulics machine (MTS Systems Corp., Eden Prairie, Minn.) with a 20 Nm reaction torque cell (Interface, Scottsdale, Ariz.) and tested to failure at a rate of 2.0 deg/sec.

The peak torque (T), torsional rigidity (TR), bulk modulus (G) and the maximum shear stress ( ) were determined through standard equations modeling each femur as a hollow ellipse. In order to compare the biomechanical parameters between different groups, the data was normalized by dividing each fractured femur value by its corresponding intact, contralateral femur value. Normalization was used to minimize biological variability and to determine the extent to which the treatment restored the biomechanical parameters of the healing fracture.

Example 1

Results

Figure 1:
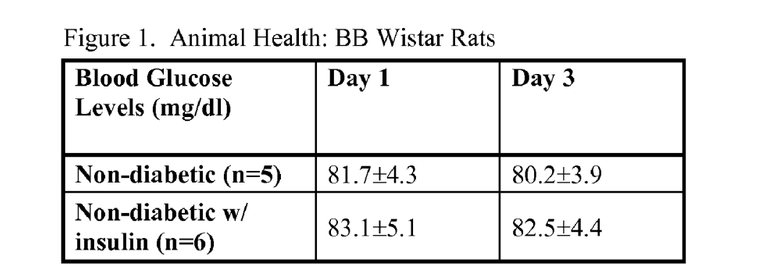
FIG. 1 is a table listing blood glucose levels for BB Wistar Rats.

The blood glucose levels between the BB Wistar non-diabetic and non-diabetic treated with local insulin groups were comparable at days 1 and 3 post-surgery (FIG. 1). These results indicate that the injection of insulin into the intramedullary canal of the fractured femur does not alter systemic blood glucose.

Figure 2:
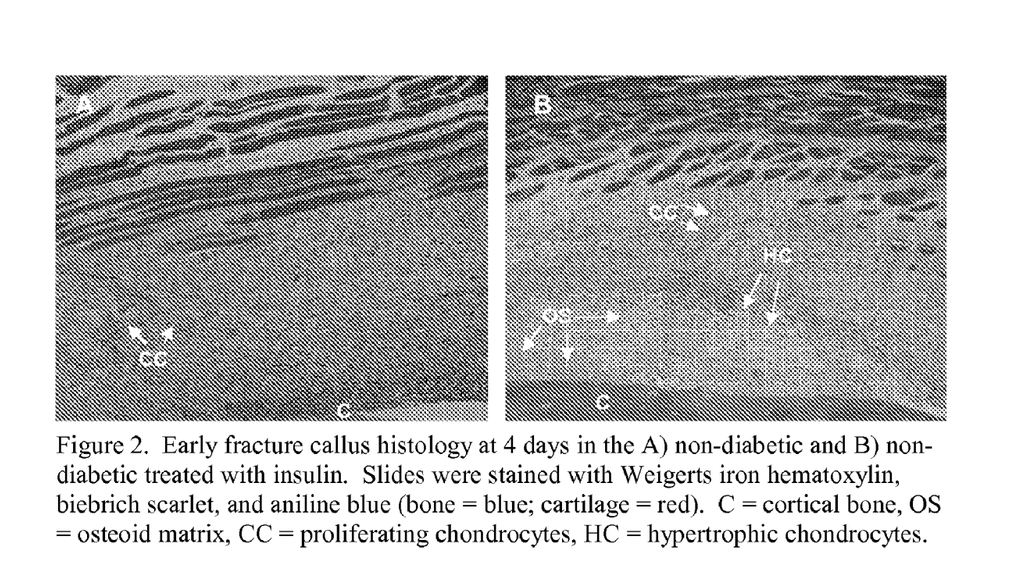
FIG. 2 provides early fracture callus histology at 4 days in the A) non-diabetic and B) non-diabetic treated with insulin.

At day 4, the insulin treated BB Wistar group showed the presence of proliferating and hypertrophic chondrocytes while the untreated BB Wistar group showed only the presence of proliferating chondrocytes (FIG. 2). In addition, osteoid matrix was present in the day 4 callus in the insulin treated group but not in the untreated group. The presence of hypertrophic chondrocytes at day 4 in the insulin treated group demonstrates an acceleration of the fracture healing process.

Figure 3:
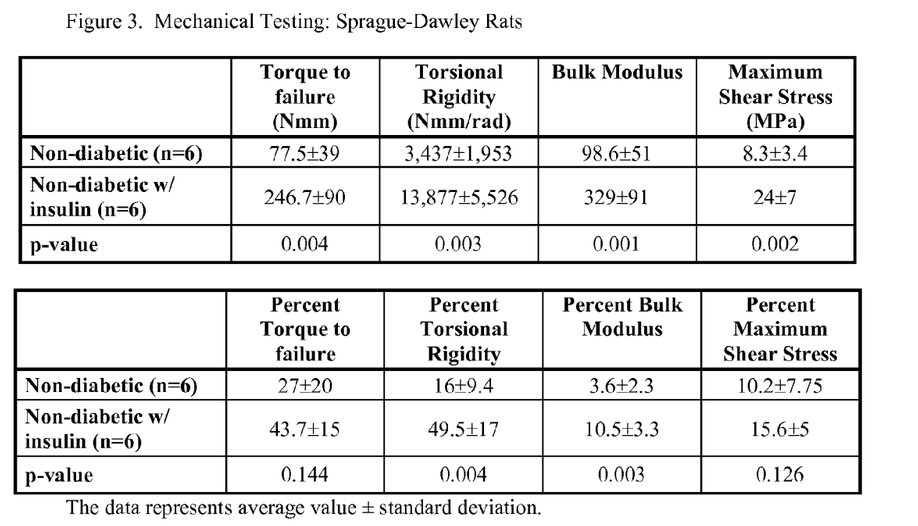
FIG. 3 is a tabulation of the results of mechanical testing in Sprague-Dawley rats.

The insulin treated Sprague-Dawley group displayed improved mechanical properties of the fractured femora compared to the untreated group (FIG. 3). The torque to failure, torsional rigidity, sheer modulus and the maximum shear stress were significantly increased with the local application of insulin. When the mechanical parameters of the fractured femora were normalized to the intact, contralateral femora, only percent torsional rigidity and sheer modulus were significantly increased in the local insulin group. However, percent torque to failure and maximum shear stress appear to be trending towards significance in the insulin treated group.

Figure 4:
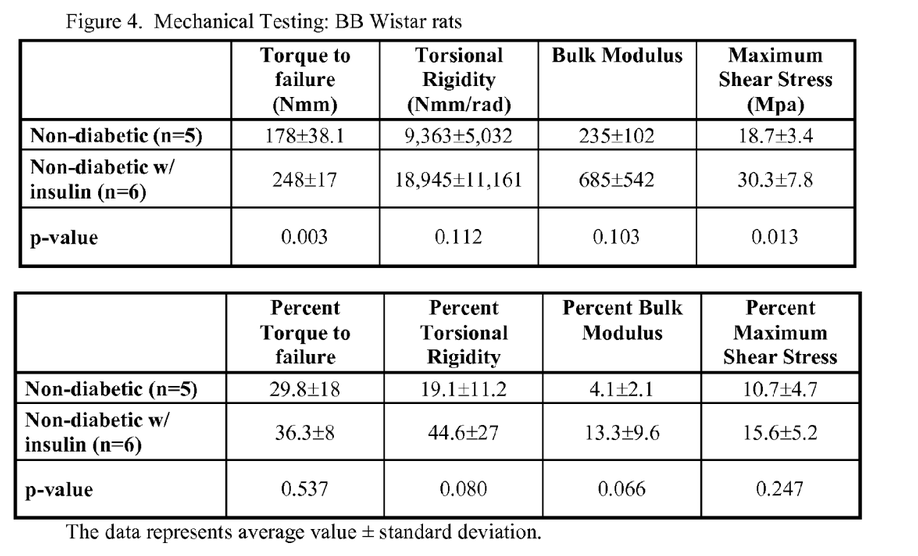
FIG. 4 is a tabulation of the results of mechanical testing in BB Wistar rats.

The insulin treated BB Wistar group displayed improved mechanical properties of the fractured femora compared to the untreated group (FIG. 4). The torque to failure and the maximum shear stress were significantly increased with torsional rigidity and sheer modulus trending towards significance in the insulin treated group. When the mechanical parameters of the fractured femora were normalized to the intact, contralateral femora, percent torsional rigidity and sheer modulus appear to be trending towards significance in the local insulin group.

Example 2

Materials and Methods

Animal Model

Non-diabetic Male and Female BB Wistar rats were obtained from the breeding colony established at UMDNJ-New Jersey Medical School Research Animal Facility derived originally from Health Canada Animal Research Division (Ottowa, Canada). The rats were housed under controlled environmental conditions and fed ad libitum. All research protocols were approved by the Institutional Animal Care and Use Committee at UMDNJ-New Jersey Medical School.

Two experimental groups were used for each species of rat: i) non-diabetic rats received 0.2 ml of carrier containing 0.1 ml saline injected into the intramedullary canal and ii) non-diabetic rats received 0.2 ml of carrier containing 0.1 ml of insulin (2.5 units) injected into the intramedullary canal. On post-surgical days 1 and 3, blood obtained from the tail vein was tested for blood glucose levels (ACCU-CHEK Advantage, Roche Diagnostics, Indianapolis, Ind.).

Fracture Model

A closed mid-diaphyseal fracture was created in the right femur using the following modification of the methods described by Bonnarens and Einhorn. Once a medial, parapatellar incision was made, the patella was dislocated laterally and the interchondylar notch of the distal femur was exposed. An entry hole was made with an 18 gauge needle and the femur was reamed. A 1 mm Kirschner wire was placed in the canal, the wire was secured in the proximal end of the femur to assure stability. Only animals that exhibited non-comminuted, transverse fractures, confirmed by radiographs, were used in this study. The animals were allowed to ambulate freely immediately post-fracture.

Surgical Procedure

General anesthesia was administered by intraperitoneal injection of Ketamine (60 mg/kg) and Xylazine (8 mg/kg). After adequate anesthesia, each rat was shaved and prepped with Betadine and 70% alcohol. A 4 mm longitudinal skin incision was made over the patella. The interchondylar notch of the distal femur was exposed after the patella was dislocated laterally. An entry hole was made with an 18 gauge needle. 0.1 ml of the treatment was administrated into the intramedullary canal. A 0.04" diameter (approximately 1.0 mm) Kirschner wire (316LVM 0.04" Dia.) obtained from Small Parts, Inc., Florida, was inserted the length of the medullary canal. More over the Kirschner wire was inserted all the way through the trochanter of the femur. After irrigation, the wound was closed with 4-0 vicryl. A closed midshaft fracture was then created unilaterally with the use of a three-point bending, Einhorn fracture machine. X-rays were taken to determine whether the fracture was of acceptable configuration.

Delivery System

Insulin was delivered directly to the fracture site using two carriers: Tri-calcium phosphate (Fluka) and calcium sulfate (J. T. Baker). Two grams of material were placed in glass vials. The vials were placed in a mechanical convection oven at 196° C. for 6 hours.

For the low dose insulin treatment group; 0.8 g of the carrier was mixed with 0.2 ml of insulin and 0.2 ml of 0.9% Sodium Chloride Irrigation, USP (Baxter Healthcare Corporation, Deerfield, Ill.). Then 0.1 ml of the mixture was placed into the intramedullary canal of each rat right femur prior to the Kirschner wire insertion.

For the positive control group 0.8 g of the carrier was mixed with 0.4 ml of 0.9% Sodium Chloride Irrigation, USP (Baxter Healthcare Corporation, Deerfield, Ill.). Then 0.1 ml of the mixture was placed into the intramedullary canal of each rat right femur prior to the Kirschner wire insertion.

Insulin Quantification

Systematic insulin levels (plasma) were measured prior to fracture and on days 2, 4 and 7 post-fracture in animals treated with intramedullary injection of carriers and insulin mixture. At day of sacrifice blood was collected by cardiac puncture from rats euthanized at days 2, 4 and 7 post-fracture. Plasma was isolated by centrifugation (1000 rpm for 30 min) and stored at −80° C. until tested.

Local insulin levels were measured from the fractured and contralateral femora on days 2, 4 and 7 post-fracture. The fractured and contralateral femora were resected and the fracture callus and mid-diaphyseal region corresponding to the fracture callus were isolated. The bone diapysis or callus was flash frozen in liquid nitrogen, pulverized and total protein extracted using an acid extraction protocol. After extraction, the supernatant was isolated by centrifugation (12,000 rpm for 10 min) and stored at −80° C. until tested.

Insulin quantification was performed in non-diabetic rats using a rat/Mouse specific insulin ELISA Kit (EZRMI-13K, Linco Research, Inc, ST. CHARLES, Mo.). The assay and analysis were performed according to the instruction of the manufacturer. Systematic insulin levels were expressed as unit per milliliter of plasma. Local insulin levels were normalized to total protein concentration measure using a bicinchoninic acid (BCA) protein assay (Pierce, Rockford, Ill.)

Mechanical Testing

Fractured and contralateral femora were resected at 4 weeks and cleaned of soft tissue. Femora were cleaned of soft tissue and the intramedullary rod was removed. Samples were wrapped in saline (0.9% NaCl) soaked gauze and stored at −20° C. Prior to testing, all femora were removed from the freezer and allowed to thaw to room temperature for three to four hours. The proximal and distal ends of the fractured and contralateral femora were embedded in Wood's metal. Torsional testing was conducted using a servohydraulics machine (MTS Systems Corp., Eden Prairie, Minn.) with a 20 Nm reaction torque cell (Interface, Scottsdale, Ariz.) and tested to failure at a rate of 2.0 deg/sec.

The peak torque (T), torsional rigidity (TR), bulk modulus (G) and the maximum shear stress ( ) were determined through standard equations modeling each femur as a hollow ellipse. In order to compare the biomechanical parameters between different groups, the data was normalized by dividing each fractured femur value by its corresponding intact, contralateral femur value. Normalization was used to minimize biological variability and to determine the extent to which the treatment restored the biomechanical parameters of the healing fracture.

Example 2

Results

Figure 8:
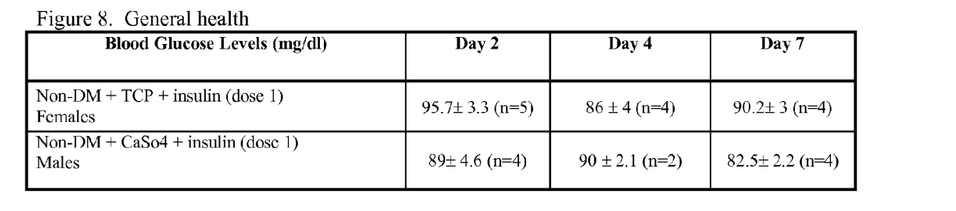
FIG. 8 is a tabulation of blood glucose levels for rats in Example 2.

The blood glucose levels between the BB Wistar non-diabetic+TCP+insulin and non-diabetic+CaSo4+insulin groups were comparable at days 2, 4 and 7 post-surgery (FIG. 8). These results indicate that the injection of insulin into the intramedullary canal of the fractured femur does not alter systemic blood glucose.

Figure 9:
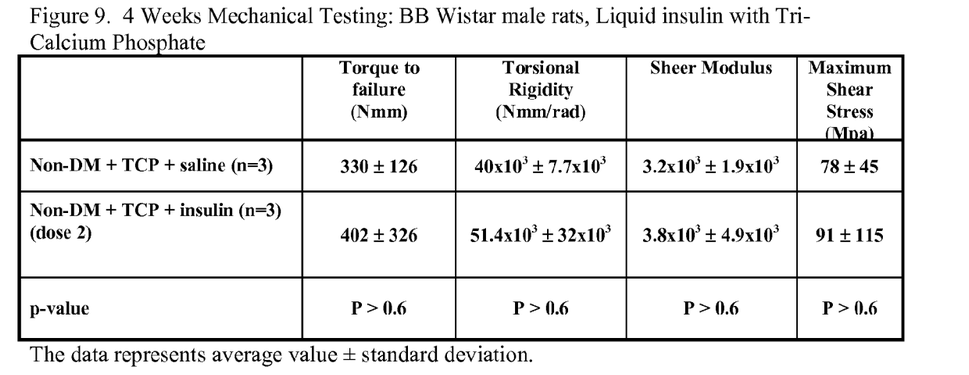
FIG. 9 is a tabulation of the results of four weeks of mechanical testing on BB Wistar male rats treated with liquid insulin and tri-calcium phosphate.

The insulin+TCP treated BB Wistar group displayed improved mechanical properties of the fractured femora compared to the Saline+TCP group (FIG. 9). The torque to failure, torsional rigidity, shear modulus and the maximum shear stress were increased with the local application of insulin.

Figure 10:
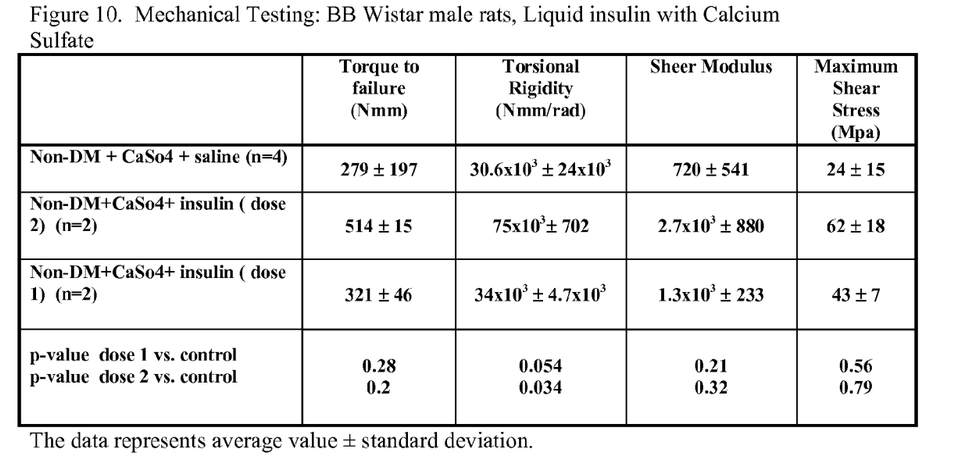
FIG. 10 is a tabulation of the results of mechanical testing on BB Wistar male rats treated with liquid insulin and calcium sulfate.

The insulin (dose 1 & dose 2)+CaSo4 treated BB Wistar group displayed improved mechanical properties of the fractured femora compared to the Saline+CaSo4 group (FIG. 10). In the insulin dose 2 group, torsional rigidity was significantly increased, also considering the small sample size of the groups the torque to failure, sheer stress, and the maximum shear stress were significantly increased. The torque to failure, shear modulus, the maximum shear stress, and torsional rigidity were trending towards significance in the insulin dose 1 group (FIG. 10).

Figure 5:
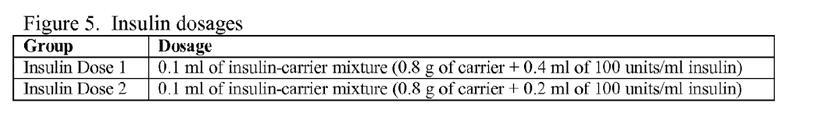
FIG. 5 is a tabulation of insulin dosages used in Example 2.
Figure 6:
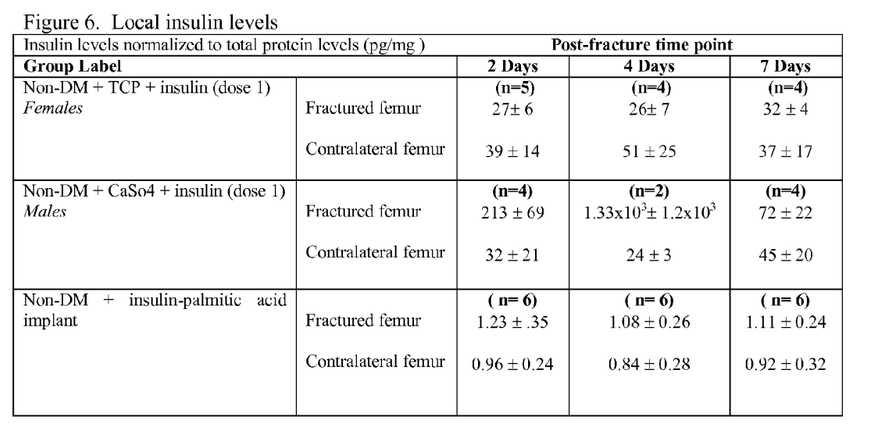
FIG. 6 is a tabulation of local insulin levels for rats in Example 2.
Figure 7:
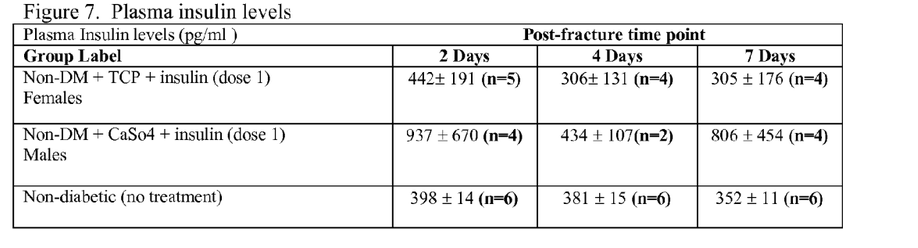
FIG. 7 is a tabulation of plasma insulin levels for rats in Example 2.

Local and plasma insulin levels at days 2, 4 and 7 were measured (FIGS. 5 and 6). Groups treated with TCP showed no significant difference in insulin levels over time either locally or in plasma.

Groups treated with insulin-CaSo4 mixture and insulin-palmitic acid implant showed a significant increase in local insulin levels, suggesting local sustained release of insulin.

Example 3

Materials and Methods

Animal Model

Non-diabetic Male BB Wistar rats were obtained from the breeding colony established at UMDNJ-New Jersey Medical School Research Animal Facility derived originally from Health Canada Animal Research Division (Ottowa, Canada). The rats were housed under controlled environmental conditions and fed ad libitum. All research protocols were approved by the Institutional Animal Care and Use Committee at UMDNJ-New Jersey Medical School.

Two experimental groups were used: i) control non-diabetic rats received one third of a blank-palmitic acid implant, which is described in U.S. Pat. No. 5,110,595, placed into the allograft segment. ii) Experimental, non-diabetic rats received one third of Insulin-palmitic acid implant, which is described in U.S. Pat. No. 5,110,595, placed into the allograft segment. On post-surgical days 1 and 3, blood obtained from the tail vein was tested for blood glucose levels (ACCU-CHEK Advantage, Roche Diagnostics, Indianapolis, Ind.).

Surgical Procedure

All rats were anesthetized using an intraperitoneal injection of a combination of Ketamine (60 mg/kg) and Xylazine (8 mg/kg). A quarter dose of this same combination was administered throughout the procedure, as a booster, if necessary. Prior to surgery, each rat received an intramuscular injection of Enrofloxacin (5 mg/kg) as a prophylactic antibiotic. A local anaesthetic, Bupivicaine (0.5 cc) was administered at the surgery site immediately prior to the start. One day post-operatively the rats were given Enrofloxacin subcutaneously (SC) and Buprenorphine SC (0.2 mg/kg).

After a surgical plane of anesthesia was induced, the right hind limb of each rat was shaved and prepared using standard aseptic techniques. The rat was then draped in a sterile manner, exposing only the right hind limb. For this surgery, an anterolateral approach was used. First, the skin over the right femur of the rat was incised with a scalpel. The vastus lateralis and biceps femoris were separated using Metzenbaum scissors down to the femur. The femur was exposed by holding back the soft tissue with specially designed spatulas, and then the periosteum was scraped away using a periosteal elevator.

A four-hole custom fabricated high density polyimide bone plate (Dupont), measuring 21.5×5.6×2.1 millimeters nominally, was positioned on the anterolateral surface of the femur. Polyimide is known for its high compressive strength as well as its outstanding wear resistance. Four holes in the bone were drilled (using a 3M Mini-Driver with a 1.3 millimeter drill bit) for #0 stainless steel flathead screws (Small Parts, Inc, Miami Lakes, Fla.). The screws have 80 threads per inch and are 5/16 inch long. All screws were inserted into the holes and tightened in place as each hole was made. After the four screws were in place, all screws except the proximal one were removed. Using the proximal screw as a pivot, the plate was swung away from the femur.

A 3 mm mid-diaphyseal defect was created in the femur using the oscillating saw attachment on the 3M Mini-Driver with a K151 blade. The plate was repositioned and the remaining three screws were put in place. Two 2-0 surgical steel monofilament cerclage wires (Ethi-pack pre-cut sutures, Ethicon Inc, Somerville, New Jersey) were braided together, and then wrapped between each pair of screws. Then, the removed bone segment was washed in triton x-100, where the periosteum was cleaned off and the marrow removed. The segment was then rinsed with saline and sterile water.

The segment was then filled with either one third of Insulin-palmitic acid implant or blank-palmitic acid implant depending on the treatment group. After that the segment was placed in the defect. The wound was closed in layers with sutures, and a topical antibiotic was applied.

Finally, x-rays were taken of the surgery site to confirm the position and type of defect. Femora that demonstrate significant communition not consistent with critical size femoral defect were excluded from the study. Post operatively, Buprenorphine was given for pain control (0.02 mg/kg) and was administered q12h and as needed based on daily observation for signs of pain and discomfort. The rats were allowed to ambulate freely post surgery because the fracture site was stabilized with plate/screws.

Histology and Histomorphometry

The femora were resected at week 6, decalcified, embedded and sectioned using standard histological techniques. After sacrifice of all animals, both right and left femurs were extracted and cleaned of extraneous soft tissue. The samples were then fixed in formalin and dehydrated in increasing concentrations of ethanol up to 100%. They were finally embedded in hard polymethylmethacrylate (hPMMA). Once embedded, the samples were cut into thin sections using a low speed diamond saw (Isomet 11-1180 Low Speed Saw, Buehler LTD, Evanston, Ill.). This resulted in properly oriented sagittal sections of approximately 300 µm. These sections were glued to microscope slides and ground (Handimet 2 Roll Grinder, Buehler LTD) to a thickness of approximately 100 µm. Finally, the samples were polished on a rotating wheel (Ecomet III polisher/grinder, Buehler LTD) with aluminum oxide particles.

The slides were stained with a combination of Stevenel's blue and Van Gieson picro-fuchsin (SVG). When stained with SVG, mineralized tissue appears orange to red, collagen fibers green to green-blue, osteoid yellow-green, and muscle fibers blue to blue-green. This is the stain of choice when using hPMMA embedding and looking at mixed tissue types.

The histomorphometry system consisted of a microscope (Olympus SZX12, Olympus Optical Co, LTD, Japan) connected via a camera (Optronics, Goleta, Calif.) to a personal computer. The Bioquant image analysis software (BQ TCW98 Version 3.40.6 ML, R & M Biometrics, Inc, Nashville, Tenn.) was used. By measuring the 7 different areas indicated below, the periosteal bone (1), endosteal bone (2), defect bone (3), and total new bone (1+2+3) was calculated. Vascularity of the defect site was calculated using the indicated areas. Using morphology, blood vessels were counted and normalized to the defect area to yield vessel density for each of the experimental groups.

Example 3

Results

Figure 11:
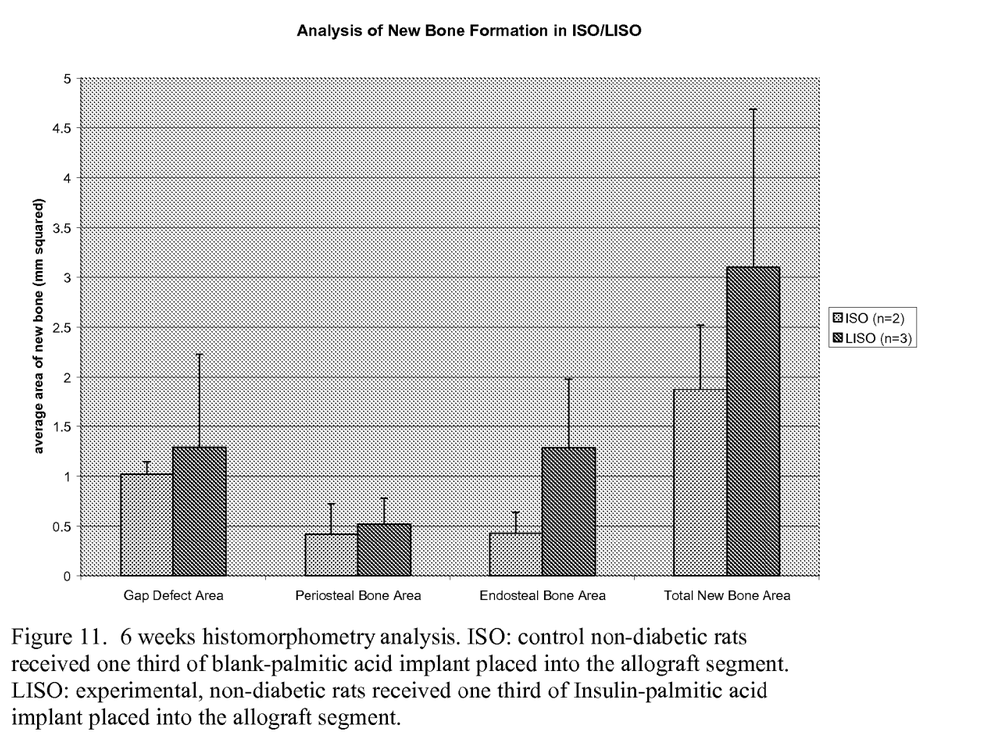
FIG. 11 is a graph providing a 6-week histomorphometry analysis.

Analysis of new bone formation in the periosteal bone (1), endosteal bone (2), defect bone (3), and total new bone (1+2+3) area demonstrated increased bone formation in the insulin-carrier group compared to carrier alone (FIG. 11).

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A method of promoting bone healing in a non-diabetic patient in need thereof comprising locally administering a therapeutically effective amount of insulin to said patient.

2. The method of claim 1, wherein said insulin is delivered via an insulin delivery system.

3. The method of claim 1, wherein said patient is afflicted with a bone condition selected from the group consisting of bone fracture, bone trauma, arthrodesis, and a bone deficit condition associated with post-traumatic bone surgery, post-prosthetic joint surgery, post-plastic bone surgery, post-dental surgery, bone chemotherapy treatment, congenital bone loss, post traumatic bone loss, post surgical bone loss, post infectious bone loss, allograft incorporation or bone radiotherapy treatment.

4. The method of claim 1, wherein said insulin is selected from the group consisting of regular insulin, isophane insulin, neutral protamine hagedorn (NPH) insulin, semilente insulin, lente insulin, ultralente insulin, insulin glargine, insulin lispro, and insulin aspart.

5. The method of claim 1, wherein said insulin delivery system comprises at least one biocompatible carrier.

6. The method of claim 5, wherein said biocompatible carrier comprises poly-lactic acid, poly-glycolic acid, copolymers of poly-lactic acid or poly-glycolic acid.

7. The method of claim 5, wherein said biocompatible carrier comprises at least one bioerodible fatty acid or a metal salt of a fatty acid.

8. The method of claim 7, wherein said fatty acid is selected from the group consisting of palmitic acid, steric acid, oleic acid, myristic acid, and metal salts thereof.

9. The method of claim 5, wherein said carrier comprises porous or non-porous calcium phosphate, porous or non-porous hydroxyapatite, porous or non-porous tricalcium phosphate, porous or non-porous tetracalcium phosphate, porous or non-porous calcium sulfate, or a combination thereof.

10. The method of claim 2, wherein said insulin delivery system comprises an article for implantation.

11. The method of claim 1, wherein said insulin delivery system comprises a coating on an article for implantation.

12. The method of claim 1, wherein said insulin delivery system comprises a bioactive bone agent.

13. The method of claim 12, wherein said method further comprises contacting the site of desired bone healing with a therapeutically effective amount of a bioactive bone agent selected from the group consisting of peptide growth factors, anti-inflammatory factors, pro-inflammatory factors, inhibitors of apoptosis, MMP inhibitors and bone catabolic antagonists.

14. The method of claim 13, wherein said peptide growth factor is selected from the group consisting of IGF (1,2), PDGF (AA, AB, BB), BMPs, FGF (1-20), TGF-beta (1-3), aFGF, bFGF, EGF, VEGF, parathyroid hormone (PTH), and parathyroid hormone-related protein (PTHrP).

15. The method of claim 13, wherein said anti-inflammatory factor is selected from the group consisting of anti-TNFα, soluble TNF receptors, ILlra, soluble IL1 receptors, IL4, IL-10, and IL-13.

16. The method of claim 13, wherein said bone catabolic antagonist is selected from the group consisting of bisphosphonates, osteoprotegerin, and statins.

17. The method of claim 1, further comprising treating said patient with at least one procedure selected from the group consisting of bone autograft, bone allograft, autologous stem cell treatment, allogeneic stem cell treatment, electrical stimulation, internal fixation, external fixation and treatment with a bioactive bone agent selected from the group consisting of IGF (1,2), PDGF (AA, AB, BB), BMPs, FGF (1-20), TGF-beta (1-3), aFGF, bFGF, EGF, VEGF, parathyroid hormone (PTH), and parathyroid hormone-related protein (PTHrP), anti-inflammatory factors such as anti-TNF.alpha., soluble TNF receptors, Mira, soluble IL1 receptors, IL4, IL-10, and IL-13, pro-inflammatory factors, inhibitors of apoptosis, MMP inhibitors and bone catabolic antagonists such as bisphosphonates, osteoprotegerin, and statins.

18. The method of claim 1, wherein said patient is afflicted with a bone condition selected from the group consisting of bone fractures and segmental defects.

19. A bone implant comprising insulin and a pharmaceutically acceptable carrier, wherein said device is adapted for localized administration of insulin to a patient in need thereof.

20. The bone implant of claim 19, wherein said carrier is comprises poly-lactic acid, poly-glycolic acid, copolymers of poly-lactic acid or poly-glycolic acid.

21. The bone implant of claim 19, wherein said carrier comprises at least one bioerodible fatty acid or a metal salt of a fatty acid.

22. The bone implant of claim 19, wherein said fatty acid is selected from the group consisting of palmitic acid, steric acid, oleic acid, myristic acid, and metal salts thereof.

23. The bone implant of claim 19, wherein said carrier comprises porous or non-porous calcium phosphate, porous or non-porous hydroxyapatite, porous or non-porous tricalcium phosphate, porous or non-porous tetracalcium phosphate, porous or non-porous calcium sulfate, or a combination thereof.

* * * * *